US009352109B2

(12) United States Patent
Wittenber et al.

(10) Patent No.: US 9,352,109 B2
(45) Date of Patent: May 31, 2016

(54) METHOD FOR SEMANTIC COMMUNICATION OF DEVICE DATA BETWEEN A SOURCE AND RECEIVING CLIENT

(75) Inventors: Jan Wittenber, Andover, MA (US); Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 452 days.

(21) Appl. No.: 13/811,922

(22) PCT Filed: Jul. 26, 2011

(86) PCT No.: PCT/IB2011/053321
§ 371 (c)(1),
(2), (4) Date: Jan. 24, 2013

(87) PCT Pub. No.: WO2012/017354
PCT Pub. Date: Feb. 9, 2012

(65) Prior Publication Data
US 2013/0118497 A1 May 16, 2013

Related U.S. Application Data

(60) Provisional application No. 61/369,777, filed on Aug. 2, 2010.

(51) Int. Cl.
*A61M 16/00* (2006.01)
*G06F 19/00* (2011.01)

(52) U.S. Cl.
CPC ........... *A61M 16/00* (2013.01); *G06F 19/3406* (2013.01); *G06F 19/3481* (2013.01); *G06F 19/345* (2013.01)

(58) Field of Classification Search
CPC ............. A61B 5/02405; A61M 16/00; A61M 16/0051; A61M 16/0057; A61M 16/0063; A61M 1/0066; A61M 16/0066; A61M 16/04; A61M 2016/0021; A61M 2016/0027; A61M 2016/003; A61M 2016/0036; A61M 2016/0039; A61M 2205/16; A61M 2205/3553; A61M 2205/3576; A61M 2205/50; A61M 2205/52; A61M 2205/8206; A61M 2205/8225; A61M 2230/10; A61M 2230/18; A61M 2230/205; A61M 2230/432; A61M 2230/46; A61M 2230/60; A61M 2230/63; A61N 1/362; A61N 1/3622; A61N 1/365; A61N 1/36585; A61N 1/39; A61N 1/3962; A61N 1/044; A61N 1/0448; A61N 1/30; A61N 1/325; A61N 1/3627; A61N 1/36592; F04D 25/166; F04D 29/052; A61K 31/135; A61K 31/16; C07C 215/60; C07C 217/62; C07C 237/30; C07C 45/305; C07C 47/277; G06F 19/3406; G06F 19/345; G06F 19/3481
USPC ............. 128/200.24, 202.22, 204.18, 204.21, 128/204.22, 204.23, 204.24, 204.26, 205.24
See application file for complete search history.

(56) References Cited

U.S. PATENT DOCUMENTS

| | | | |
|---|---|---|---|
| 6,349,724 B1 * | 2/2002 | Burton et al. ............. | 128/204.18 |
| 2002/0143290 A1 | 10/2002 | Bui et al. | |
| 2003/0135087 A1 | 7/2003 | Hickle et al. | |

(Continued)

FOREIGN PATENT DOCUMENTS

| | | |
|---|---|---|
| CN | 101496923 | 8/2009 |
| EP | 1102035 A2 | 5/2001 |
| WO | 2009023634 A2 | 2/2009 |

OTHER PUBLICATIONS

Garguilo, J. J., et al.; Moving Toward Semantic Interoperability of Medical Devices; 2007; Joint Workshop on High Confidence Medical Devices, Software and Systems and Medical Device Plug-and-Play Interoperability; pp. 13-19.

*Primary Examiner* — Annette Dixon

(57) ABSTRACT

A treatment delivery system includes one or more medical therapy delivery devices (34) which deliver medical treatment or therapy to a patient, and one or more medical devices (10) which monitor results of the delivered medical therapy or treatment, clinical information, laboratory information, and health record information. The medical treatment delivery device has a proprietary communications protocol. A medical therapy delivery controller (18) semantically communicates among the medical device(s) and one or more medical treatment delivery devices. The controller has a user input (32) by which a user inputs therapy objectives in other than the proprietary communications protocol and a control processor (26) which generates treatment delivery device control commands, receives treatment or therapy results from a medical device (10), and adaptively adjusts the control commands based on the received treatment results. The control processor accesses a clinical decision support system (41), determines a physiological state of the patient from the received treatment results, and adjusts one of the therapy objectives and the control commands in accordance with input from the clinical decision support system.

10 Claims, 5 Drawing Sheets

(56) References Cited

U.S. PATENT DOCUMENTS

| | | |
|---|---|---|
| 2005/0066002 A1 | 3/2005 | Teres et al. |
| 2007/0050780 A1 | 3/2007 | O'Dea et al. |
| 2008/0229281 A1 | 9/2008 | Requardt et al. |
| 2009/0028185 A1 | 1/2009 | Doerr et al. |

* cited by examiner

METHOD FOR SEMANTIC COMMUNICATION OF DEVICE DATA BETWEEN A SOURCE AND RECEIVING CLIENT

CROSS REFERENCE TO RELATED APPLICATIONS

This application is a national filing of PCT application Serial No. PCT/IB2011/053321, filed Jul. 26, 2011, published as WO 2012/017354A2 on Feb. 9, 2012, which claims the benefit of U.S. provisional application Ser. No. 61/369,777 filed Aug. 2, 2010, which is incorporated herein by reference.

The present application relates to a system and method for semantic communication of device data between a source and a receiving client. It finds particular application in improving the communication semantics of medical therapy delivery or monitoring devices and will be described with particular reference thereto.

Presently, various medical devices such as ventilators, medication and nutrition administration devices (i.e. feeding or IV pumps), pacemakers, body temperature controllers, anesthesia delivery, home monitoring, photo therapy, image system gating, and the like, communicate between each other in a variety of proprietary and open communication schemas when delivering therapy to a patient. Many manufacturers of these devices use different naming conventions (nomenclature) to represent the method and modes by which they deliver therapy to differentiate their devices when in fact they are delivering the same therapy. In addition, these medical devices have sophisticated controls which permit numerous details of the delivery to be selected. The differences in the way these devices represent the method and modes by which they deliver therapy produce unsafe and ambiguous environments between therapy objective and the patient machine interface. Because of this, there is difficulty in conveying the intent of the clinician, particularly as modified in light of current physiological conditions of the patient, to the detailed control of the device(s).

Problems also exist when such devices are used in conjunction with each other in closed loop or partial closed loop control and safety interlock configurations. In such configurations, the devices must understand the same semantics in order to provide a safe therapy environment and complete situational awareness. In many cases, the data communicated from one device needs to be translated to an ontology that the other device understands, which can produce ambiguous communication between the devices resulting in unsafe therapy conditions.

The present application provides a new and improved method for semantic communication for device data between a source and a receiving client which overcomes the above-referenced problems and others.

In accordance with one aspect, a medical therapy delivery controller is provided. The controller controls operation settings of a medical therapy delivery device which has a heterogeneous or proprietary communication protocol. The controller includes a user input by which a user inputs therapy objectives in other than the proprietary communications protocol. The controller also has a control processor which generates therapy delivery device control commands, receives treatment results from another medical device or patient monitor, and adaptively adjusts the control commands based on the received treatment results. The control processor may be either in the medical device or monitor, or in another unit.

In accordance with another aspect, the control processor further accesses a clinical decision support system. The control processor determines a physiological state of the patient from the received treatment results and adjusts at least one of the therapy objectives and the control commands in accordance with input from the clinical decision support system.

In accordance with another aspect, a treatment delivery system is provided which includes at least one treatment delivery device that delivers medical treatment to a patient, at least one device which monitors the results of the delivered medical treatment, and at least one medical therapy delivery controller.

In accordance with another aspect, a method of semantic communication between a plurality of medical devices, in which at least two devices are participating in a common therapy, communicate semantically. The results of medical treatment of a patient who is receiving delivered medical therapy or treatment are collected with a monitoring device. The results are indicative of the effects of the therapy on the patient's physiological state. One or more medical treatment delivery devices delivery medical therapy to the patient in accordance with a therapy objective communicating semantically among the monitoring and medical treatment delivery devices and the therapy objective, the semantic communication including the results of the medical therapy and the therapy objective for the patient. One or more operational settings of the one or more medical treatment delivery devices is adjusted based on a semantic communication(s).

One advantage resides in clear conveyance of the therapy objective of the clinician to the detailed control of the patient device interface(s).

Another advantage resides in providing safe and unambiguous environments between the therapy objective and the patient device interface during the delivery of therapy.

Another advantage resides in the unambiguous communication of device data between a plurality of patient device interfaces.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically illustrates a medical treatment delivery system;

While the present disclosure of a system and method for semantic communication is illustrated as being particularly applicable to a ventilator interface, it should be appreciated that the present disclosure can be applied to any medical therapy delivery or medical monitoring device which has a series of settings, driving function, and device and/or patient results from the therapy device, such as IV or medication or nutrition administration systems, pacers/defibrillators, thermal control systems, anesthesia delivery systems, and the like.

In a preferred embodiment, a system and method for semantic communication is illustrated which is able to communicate between various medical devices such that the relationships of expected device settings and observed patient results are based on common base functions (primitives), relationships between, and transfer functions relating to the primitives. The semantic communication allows each therapy epoch or event, such as a patient's breath, to be broken down into an array of implicit or explicit primitives and transfer functions describing the intended relationship of primitives and the actual delivered results. In order to facilitate semantic understanding of the primitives and transfer functions between various medical devices, the primitives and transfer functions are named or tagged based on a harmonized naming standard or a particular medical device manufacturer naming standard.

For example, in the case where a clinician wants to control at a high level the delivery of therapy from a ventilator, the clinician would select the delivered oxygen volume, flow rate, pressure, and the like being delivered to the patient. The clinician would also input statements relating to the various primitives, such as gas flow, volume, and pressure, how the selected primitives should relate to each other, acceptable ranges, over time, and how the selected primitives should vary with changes in the patient's physiological state, and the like. From the combination of the statements, primitives, and measurements of the patient's physiological state, transfer functions are generated. In the ventilator example, the transfer function may be the difference between the intent of the medical therapy and the actual delivery of oxygen in each breath. Open, partial, and closed feedback loops modify the operating parameters of the ventilator in order to maintain the delivery of oxygen to the patient, or CO2 removal from the patient, within the limits and parameters set forth by the clinician, while maintaining other cardiovascular or physiologic parameters within acceptable limits, through the use of the statements and primitives.

Figure 1:
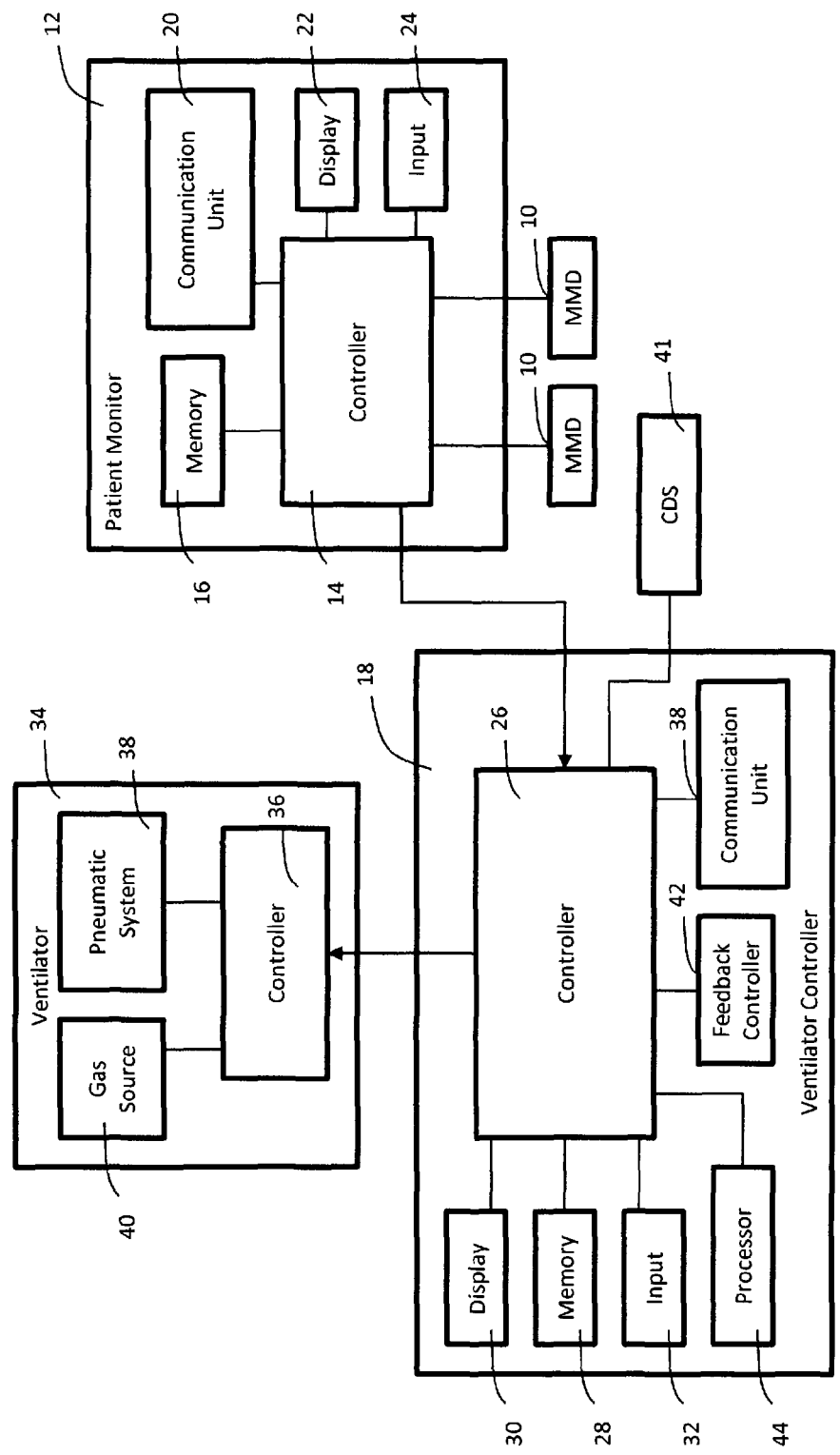

Such a system and method for semantic communication is particularly advantageous in a medical treatment delivery system as shown in FIG. 1. With reference to FIG. 1, a patient (not shown) interacts with various medical devices 10 that measure physiological parameters of the patient and generate physiological data indicative thereof, clinical information, laboratory information, medication administration, historical physiologic, and other health record information. These medical and information devices 10 may include an electrocardiographic (ECG) instrument with internal or surface ECG electrodes, IV fluid or medication or nutrition pumps, pleural pressure, blood pressure, abdominal pressure, and cardiac output sensors, SpO2 sensors, SO2 and SaO2 sensors, pH sensors, PaO2 sensors, FIO2 sensors, ETCO2 sensors, pulse sensors, thermometers, respiratory sensors, exhaled gas sensors, other therapy measures and the like. The medical monitoring devices may also include ventilator time, flowmeters, resistance and compliance sensors, gas mixture and pressure sensors to measure patient airway pressure, flow and resistance in the case of ventilation therapy.

Other therapy applications have other medical and information devices in use. For example, if cardiac pacing is the therapy application in mind, the epoch is each cardiac beat. The intended therapy can be related to cardiac output, ejection fraction, preload, or other inputs such as patient assessment of dyspnea or shortness of breath. The therapy primitives can be pace pulse impulse duration, timing, current, waveform characteristics, and the like. Primitives can be interval and segment measures related to each ECG lead, maximum and minimum ST location, conduction vectors, beat to beat averages and wave pattern morphology, and overall beat to beat pressure wave timing, morphology, and perfusion flow.

Another therapy application to which to this semantic approach can be applied is thermal regulation and therapeutic hypothermia. In this case the therapy epoch is defined as duration based on the reason for therapeutic hypothermia. In this application, the primitives include core temperature, cooling trajectory, target temp, expected duration, as well as metabolic and physiologic feedback such as lactate, O2 consumption, and EEG activity to name a few.

Other medical devices 10 can be associated with a patient, and not all of the above-mentioned medical devices 10 have to be associated with a patient at any given time. It should be appreciated that while only two medical devices 10 are illustrated, more medical monitoring devices or health record laboratory findings, medication administration or other clinical information and devices are contemplated. As used herein, medical monitoring devices signify data sources indicating patient health, treatment delivery device status, or the like. Sensors for receiving signals from the medical device 10 and for optionally performing signal processing on such signals are embodied in the illustrated embodiment as a multi-functional patient monitor device 12, or may be embodied partly or wholly as on-board electronics disposed with one or more of the medical devices 10 or so forth. It should also be appreciated that the medical devices 10 and the patient monitor 12 could also be embodied into a single device. The patient monitor 12, for example, may be a monitor that travels with the patient, such as the transmitter of an ambulatory patient worn monitoring system, or the like.

The medical devices 10 transmit the generated physiological data via a body coupled network, Zigbee, Bluetooth, wired or wireless network, or the like to a controller 14 of the patient monitor 12. The patient monitor 12 serves as a gathering point for the physiological data measured by the medical devices 10, and provides temporary storage for the data in a memory 16. The collected physiological data is concurrently transmitted to a controller 14 in the patient monitor 12 which then transmits the physiological data in a semantic communication to a ventilator controller 18 where the physiological data is displayed and stored. The semantic communication contains information relating to the intent of the medical therapy and information relating to the results of the delivered therapy. The semantic communication also includes an array of implicit or explicit primitives and transfer functions describing the intended relationship of primitives and the actual delivered results, such as the physiological data.

Optionally, a communication unit 20 controlled by the controller 14 transmits the physiological data in the semantic communication to the ventilator controller 18. The controller 14 of the patient monitor 12 also controls a display 22 to display the measured physiological data received from each of the medical monitoring devices 10 in the patient monitor display 22. The patient monitor 12 also includes an input device 24 that allows the clinical operator or user, such as a system administrator, to view, manipulate, and/or interact with the data displayed on the display 18. The input device 24 can be a separate component or integrated into the display 18 such as with a touch screen monitor. The controller 14 may include a processor or computer, software, or the like.

A control processor 26 of the ventilator controller 18 receives the semantic communication from the patient monitor 12 and stores the physiological data in a memory 28. The control processor 26 also controls a display 30 of ventilator controller 18 to display the physiological data received from the patient and the semantic communication received from the patient monitor 12 in the display 30. The control processor also forwards the physiological data to a clinical decision system (CDS). The ventilator controller 18 also includes an input device 32 that allows a clinician to input various ventilator settings and the objectives or intent of the medical therapy of the patient on a ventilator 34 using generic terminology. The ventilator settings include delivered oxygen volume, flow rate, pressure, open loop setting, closed loop setting, partial closed loop settings, and the like being delivered to the patient. The ventilator settings also include the different modes of ventilator operation including continuous positive airway pressure, synchronized intermittent mandatory or machine ventilation, and the like. The clinician may also input, using the input device 32, statements native to the device, relating to various primitives, such as flow, volume, and pressure, how the selected primitives should relate to each other, acceptable ranges, and how the selected primitives should vary with changes in the patient's physiological state, and the like. The input device also allows the user, such as administrative personal, to view, manipulate, and/or interface with the data displayed on the display 30. The input device 32 can be a separate component or integrated into the display 30 such as with a touch screen monitor. One example of the input includes: "maintain SpO2>x % while minimizing Fio2 to 0.35, and PSV to 5 cmH2O to a max of FiO2 85% and PSV 27 cmH2O according to the Fio/SpO2 function F(FiO2/SpO2 (t))=blabla, and F(FiO2/PSV (t))=blablabla".

The inputted ventilator settings and the intent of the medical therapy are concurrently transmitted to the control processor 26 in the ventilator controller 18 which then transmits the ventilator settings and the intent of the medical therapy in a semantic communication to a controller 36 in a ventilator 34 which has a proprietary communications protocol. The control processor adapts the generic (or proprietary) input from the monitor and the generic objectives from the input 32 into appropriate control commands for the ventilator or other treatment delivery device. Although shown as separate functions, it is to be appreciated that these functions can be performed by a common processor or controller. Optionally, a communication unit 38 controlled by the control processor 26 transmits the ventilator settings and the intent of the medical therapy in the semantic communication to the ventilator 34. The control processor 36 of the ventilator 34 controls a pneumatic system 38 to control the flow and pressure of gas delivered from a gas source 40 to a patient's airway in accordance with the ventilator settings and of the intent of the medical therapy. It should also be appreciated that the ventilator 34 and the patient monitor 12 could be partially or fully embodied into a single device. The ventilator 34, for example, may be a ventilator 34 which measures one or more of the physiological parameters of the patient which transmits the physiological data in a semantic communication to the ventilator controller 18, or the like.

The control processor 26 of the ventilator controller 18 compares the intent of the medical therapy and the results of the delivered medical to determine if the results from the delivered therapy are within the parameters and limits of the intent of the medical therapy. If the results of the delivered medical therapy are not within the parameters and limits of the intent of the medical therapy, the control processor 26 of the ventilator controller 18 adjusts the closed loop and partial closed loop settings of the ventilator 34 in order for the results of the delivered medical therapy to be within the limits and parameters of the intent of the medical therapy. Control settings may also be changed if the controller determines that a more optimal set of feedback values can be achieved within constraints defined by the statement of therapeutic intent (this is commonly referred to as "optimization", for example, to achieve a maximal flow rate at the lowest positive pressure in a given or variable period of time). The control processor 26 also accesses a clinical decision support system (CDS) 41, which may be internal to the ventilator controller 18, to the patient monitor (12) or external to both devices. The CDS adapts the therapy objectives or the ventilator control commands in accordance with best medical practices for a patient with the patient's current physiological or clinical state or upon gaining new knowledge, such as clinical history, laboratory information, medication administration, and other health record information. In this manner, the therapy adapts or evolves as the patient's physiological state improves or deteriorates over time. The control processor 26 also controls the display 30 of the ventilator controller 18 to display an alarm condition when the results from the delivered medical therapy are not within the parameters and limits of the intent of the medical therapy to indicate that clinician intervention is required.

Optionally, a feedback controller 42 of the ventilator controller 18 compares the intent of the medical therapy and the results of the delivered medical treatment to determine if the results from the delivered therapy are within the parameters and limits of the intent of the medical therapy. The feedback controller 42 also adjusts the closed loop and partial closed loop settings of the ventilator 34 and/or controls the display 30 of the ventilator controller 18 to display an alarm condition when the results from the delivered medical therapy are not within the parameters and limits of the intent of the medical therapy to indicate that clinician intervention is required.

The control processor 26 of the ventilator controller 18 also includes a processor 44, for example a microprocessor or other software controlled device configured to execute semantic communication and ventilator control software for performing the operations described in further detail below. Typically, the semantic communication and ventilator control software is stored in is carried on other tangible memory or a computer readable medium 28 for execution by the processor. Types of computer readable media 28 include memory such as a hard disk drive, CD-ROM, DVD-ROM and the like. Other implementations of the processor are also contemplated. Display controllers, Application Specific Integrated Circuits (ASICs), and microcontrollers are illustrative examples of other types of component which may be implemented to provide functions of the processor. Embodiments may be implemented using software for execution by a processor, hardware, or some combination thereof.

The semantic communications includes arrays of primitives, statements, event summaries, and event tags. The primitives are constructed by identifying a driving function for each therapy epoch, an optimizing function for the therapy epoch, and accepted functions for the therapy epoch. The statements are constructed from each base function which contains an implicit or explicit statement with enumeration or a conditional statement relating to the therapy epoch. The statements also contain the transfer function information relating to the primitives. The event summaries each include an intended and delivered or resulting component. The event summaries are generated from the primitives and statements. The event tag includes an event type tag which is based on either a harmonized naming standard or manufacture's declaration.

With reference to FIGS. 2A-2D, the semantic communications includes an event tag 100, with a unique reference to each event reported (breath ID) such as patient breath, and a mode of operation 102 of the medical device delivering the medical therapy. As used herein, mode of operation signifies the different methods, patterns, or modes that the medical therapy devices deliver, including continuous positive airway pressure, synchronized intermittent machine ventilation, and the like. The semantic communications also include the intent of the medical therapy 104 and the result of the delivered medical therapy 106. The intent of the medical therapy 104 includes data relating to the medical therapy device, such as the delivered oxygen volume, flow rate, pressure, medical therapy device settings, and the like being delivered to the patient on the ventilator. The intent of the medical therapy 104 also includes data relating to the patient, such as how the selected primitives should relate to each other, acceptable ranges, and how the selected primitives should vary with changes in the patient's physiological state, and the like. The result of the delivered medical therapy 106 includes data relating to the patient's physiological state and the medical therapy device's delivery results, such as the output pressure, flow and volume of the ventilator.

To facilitate computation of the physiologic applications, modes, variables, control loops, and the like, that can be defined as transfer functions, for example, as components in Laplace Transforms of partial differential equations representing temporal relationships among pressure, flow, and volume. For example, objective breath shapes may be defined based on demographic and/or morbidity types or attributes, such as adult, pediatric, or neonatal characteristics; or COPD (Chronic Obstructive Pulmonary Disease) profiles based on salient parameters such as pulmonary mechanics, physiologic system response, and patient effort.

Figure 2A:
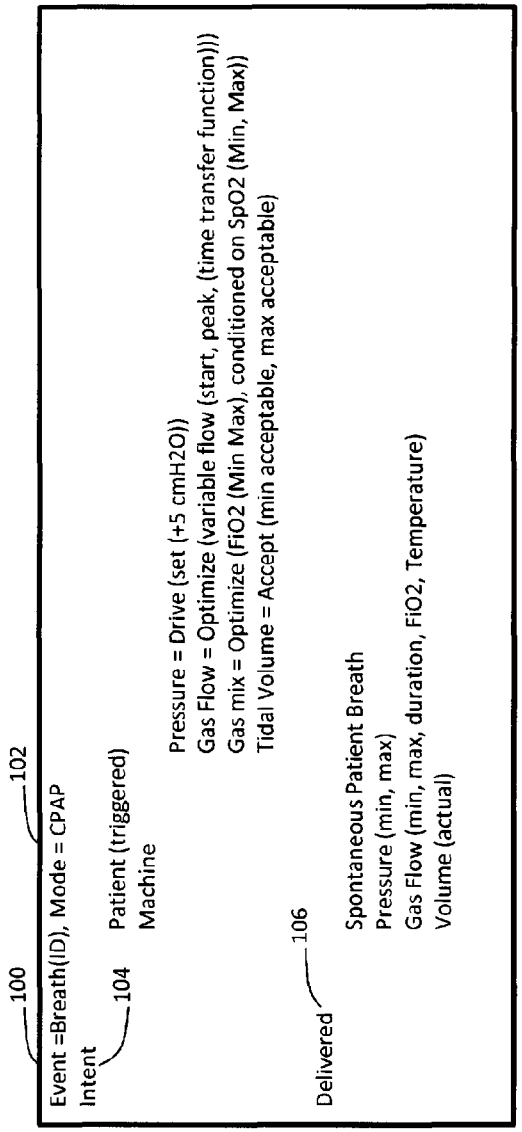
FIGS. 2A-2D illustrate four examples of semantic communication for a ventilator.
Figure 2B:
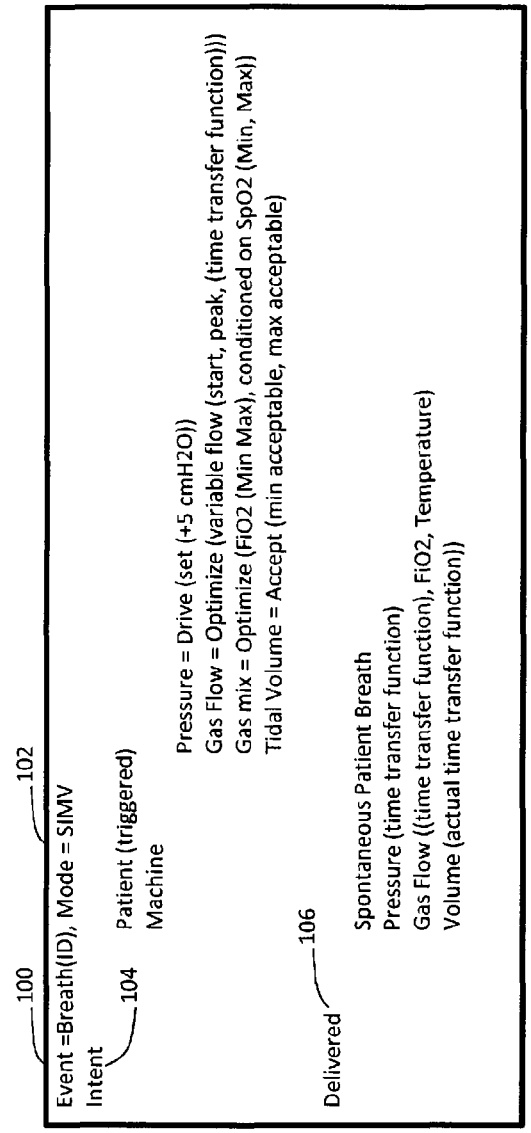
Figure 2C:
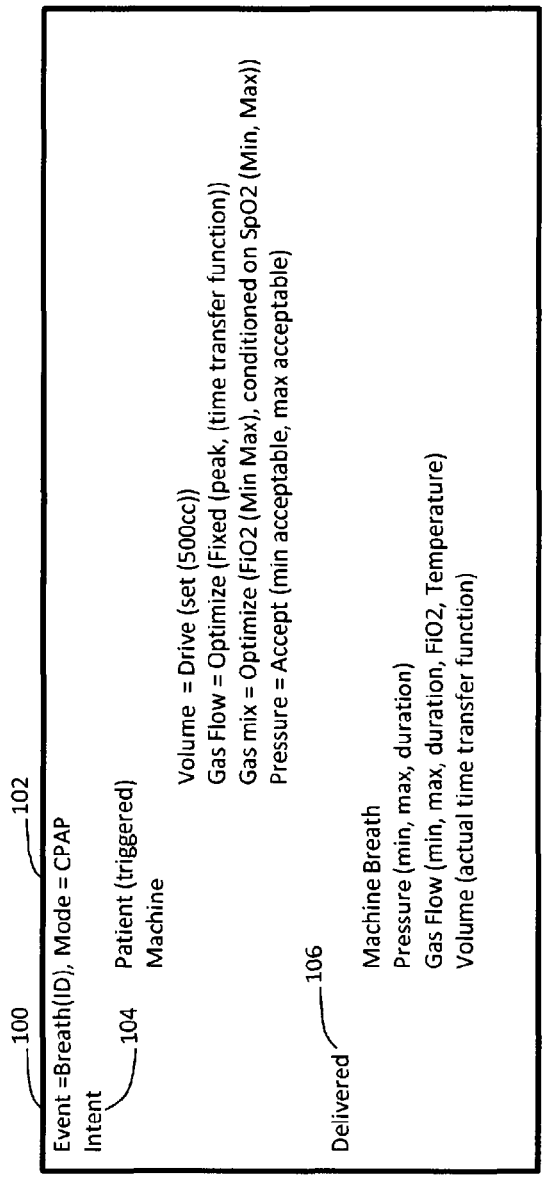

FIGS. 2A and 2C illustrates an example of a semantic communication for a ventilator providing continuous positive airway pressure in a CPAP mode. In this example, the driving function is airway pressure. The driving function is delivered by the optimizing function or the machine gas flow in this example. The resulting function is patient expired volume. The semantic communication also indicates that the patient initiates each breath (i.e. there is no machine cycling based on delivered pressure or volume).

Figure 2D:
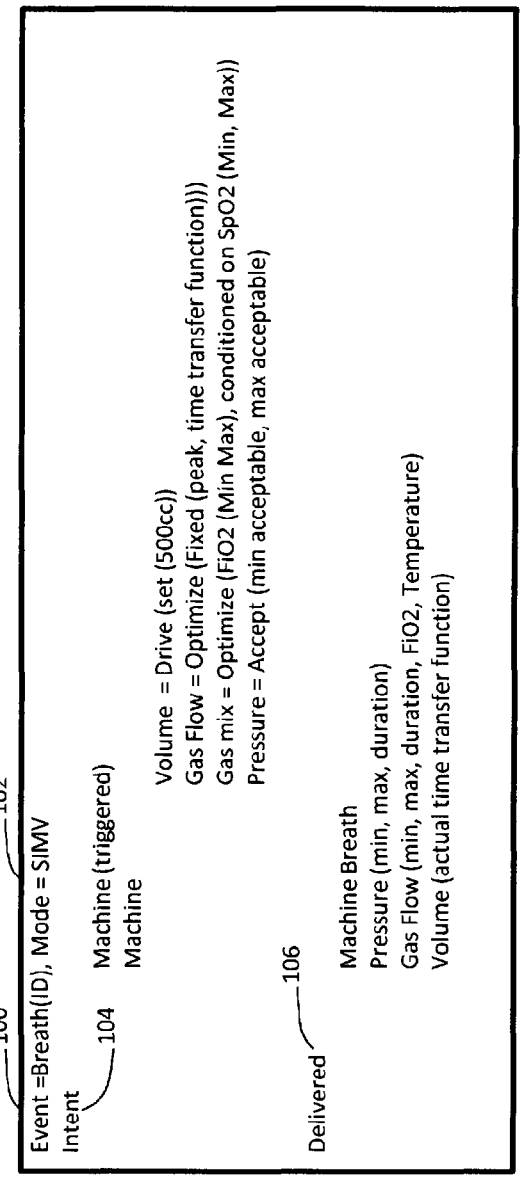

FIGS. 2B and 2D illustrate examples of semantic communications for ventilators providing synchronized intermittent machine ventilation. In these examples, the ventilator is programmed to deliver a certain number of volume cycled breaths per minute to a maximum permissive pressure with a predefined flow pattern. When the machine breath is not intended the patient is allowed to breathe as if they were on basic CPAP, i.e., patient initiated breathing. Conditional and/or context-sensitive statements may be included as needed to accommodate configuration variations such as "Automatic Tube Compensation (ATC)".

Figure 3:
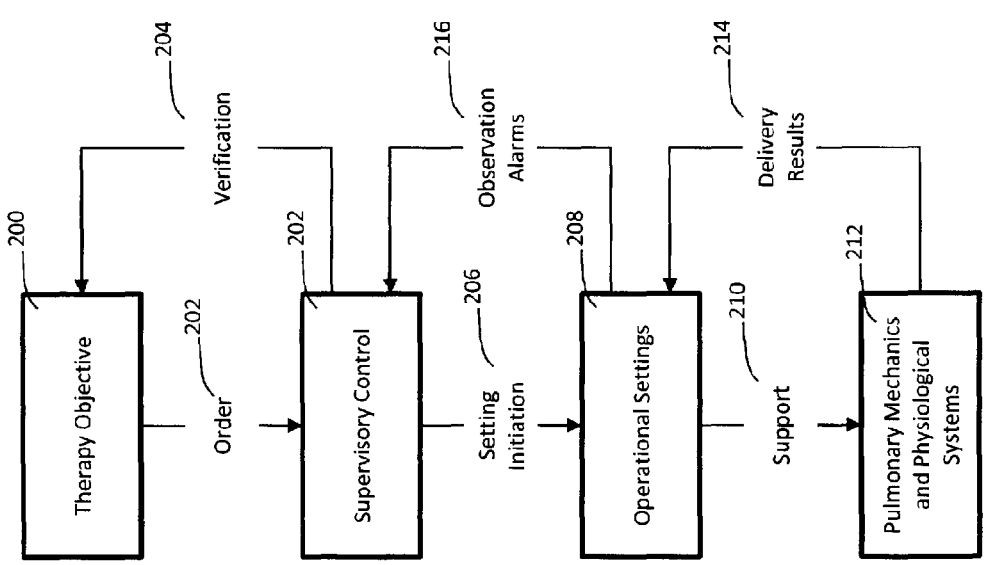
FIG. 3 is a flowchart illustrating operation of the system.

FIG. 3 illustrates operation of the treatment delivery system. In a step 200, a therapy objective or intent of the medical therapy is inputted by a clinician. In a step 202, the therapy objective is ordered by the clinician and transmitted to a supervisory control. In a step 204, the therapy objective is verified by the supervisory control. In a step 206, the supervisory control initiates the settings of the medical therapy device for the therapy objective. In a step 208, the operational settings are inputted into the medical therapy device for the therapy objective. The operational settings are utilized to support the medical therapy device in delivering the medical therapy in a step 210. In a step 212, the pulmonary mechanics and physiological systems are monitored to determine the results of the delivered medical therapy. The operational settings of the medical therapy device are then adjusted based on the delivery results of the medical therapy in order to deliver the medical therapy within the parameters and limits of the therapy objective in a step 214. In a step 216, observation alarms generated if the delivery results of the medical therapy are outside the parameters and limits of the therapy objective are transmitted to the supervisory control.

Figure 4:
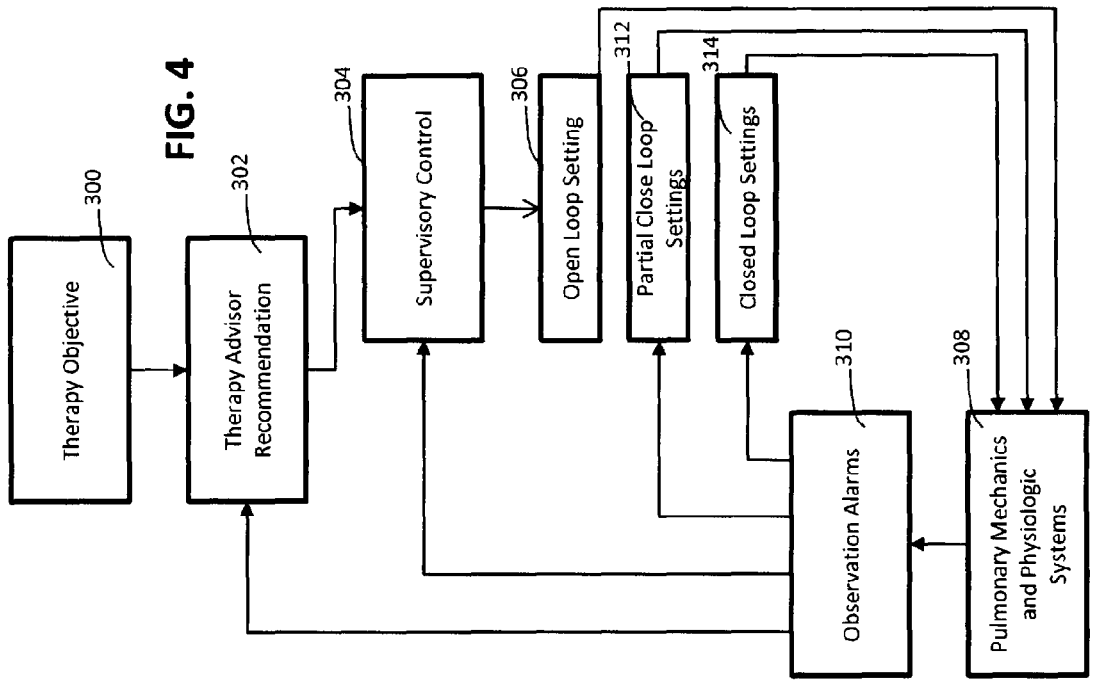
FIG. 4 is a flowchart illustrating operation of the system.

FIG. 4 illustrates operation of the treatment delivery system. In a step 300, a therapy objective or intent of the medical therapy is inputted by a clinician. In a step 302, the therapy objective is transmitted to a therapy advisor which recommends a proper medical therapy for the therapy objective. In a step 304, the medical therapy is transmitted to a supervisory control. In a step 306, the supervisory control adjusts the settings of the medical therapy device for the medical therapy. In a step 308, the pulmonary mechanics and physiological systems are monitored to determine the results of the delivered medical therapy. Observation alarms are generated if the delivery results of the medical therapy are outside the parameters and limits of the therapy objective in a step 310. The observation alarms are transmitted to the therapy advisor, the supervisor control, and partial closed loop and closed loop settings. In a step 312, the partial closed loop settings are adjusted based on the delivery results of the medical therapy in order to deliver the medical therapy within the parameters and limits of the therapy objective. In a step 314, the closed loop settings are adjusted based on the delivery results of the medical therapy in order to deliver the medical therapy within the parameters and limits of the therapy objective from breath to breath as well as over the long term, e.g., entropy can be tracked and controlled.

Figure 5:
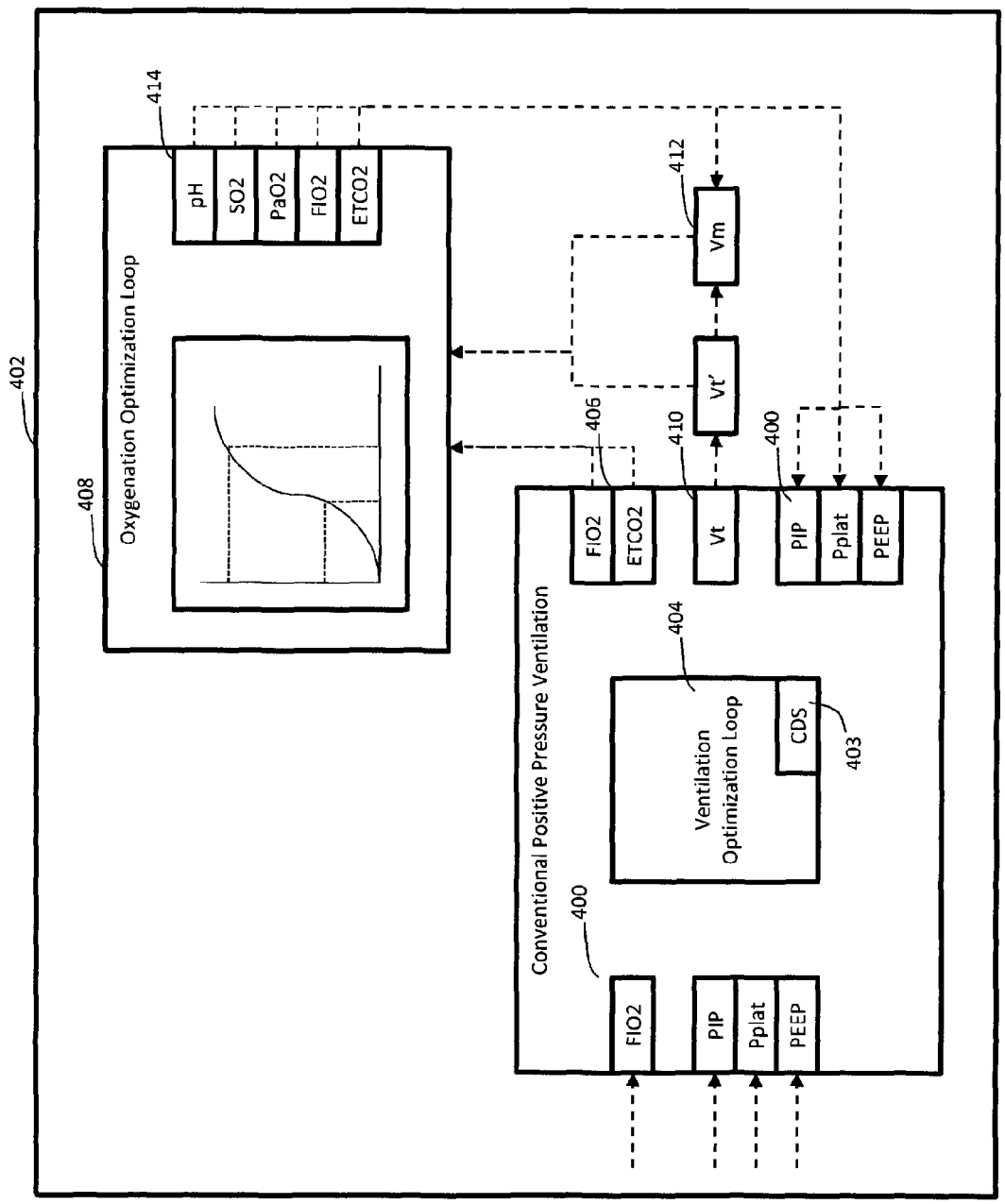
FIG. 5 illustrates a ventilator feedback controller.

With reference to FIG. 5, each therapy epoch may have multiple feedback paths which are independent from each other but are coupled and optimized. Here a plurality of data inputs 400 including a fractional inspired oxygen concentration, peak inspiratory pressure, plateau pressure, peak end expiratory pressure, clinical information, laboratory information, medication administration, historical physiological and other health record information, and the like are inputted into a ventilator feedback controller 402. The data inputs 400 are utilized by a ventilation optimization loop 404 to optimize the operational settings of the ventilator in order to provide the proper medical therapy based on the data inputs 402 and intent of the therapy. The ventilation optimization loop 404 outputs a plurality of data outputs 406 including a fractional inspired oxygen concentration, an end tidal carbon dioxide concentration, and the like to a oxygenation optimization loop 408 which optimizes the oxygenation of the ventilator in order to provide the proper medical therapy based on the data inputs 402. For example, a clinical decision system 403 is included, e.g., including a decision tree, which maps the patient's improving or deteriorating physiological state to appropriate evolving treatment levels. The ventilation optimization loop 404 also outputs a tidal volume. The tidal volume 410 is combined with a minute volume 412 of the ventilator and input along with the data outputs 406 to the oxygenation optimization loop 408. A plurality of physiological parameters 414 including pH, a saturation level of oxygen, a partial pressure of CO2, a fractional inspired oxygen concentration, an end tidal carbon dioxide concentration, and the like, of the patient resulting from the delivered medical therapy are then inputted to ventilation optimization loop 404 which then optimizes the operational settings of the ventilator in order to provide the proper medical therapy based on the physiological parameters 414.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical therapy delivery system comprising:
   a treatment delivery device configured to deliver medical treatment to a patient;
   a medical device configured to collect physiological data;
   a patient monitor configured to collect the physiological data, determine results of the delivered medical treatment, and transmit the physiological data and the results in a semantic communication, the semantic communication including an array of primitives and transfer functions describing the relationship of the primitives and the determined results;
   a user input device configured to input a therapy objective;
   a controller configured to receive the semantic communication and the therapy objective and adaptively adjust operation settings of the treatment delivery device based on the semantic communication and the therapy objectives.

2. The system according to claim 1, wherein the controller receives at least one of metabolic data, physiological data, clinical information, laboratory information, and health record information indicative of a current physiological state of the patient, further including:
   a clinical decision support system configured to adapt at least one of the therapy objective and the operational settings in accordance with the received at least one of the patient's current physiological state, clinical information, laboratory information, and health record information.

3. The system according to claim 1, wherein the patient monitor includes a processor configured to receive the collected physiological data and configure the semantic communication.

4. The system according to claim 1, wherein the treatment delivery device includes at least one of: IV or medication administration systems, nutritional feeding devices, ventilators, pace makers/defibrillators, thermal control systems, phototherapy delivery systems, radiation delivery systems, imaging systems, home monitoring, and anesthesia delivery systems.

5. The system according to claim 1, wherein the controller is further configured to adjust closed loop and partial closed loop settings of the treatment delivery device.

6. The system according to claim 1, wherein the therapy objective includes at least one of: data relating to the medical device's delivery of medical therapy to the patient including the relationship of various operation settings, acceptable ranges and parameters, and how the selected operation settings should vary with changes in the patient's physiological state.

7. A method delivering medical treatment, the method comprising:
   with a medical monitor device, collecting physiological data and delivering results of a delivered medical treatment, and transmitting the data and the results in a semantic communication, the semantic communication including an array of primitives and transfer functions describing a relationship between the primitives and the determined results;
   with a controller, receiving the semantic communication and a therapy objective from a user input device and adaptively adjusting operational settings of a medical treatment delivery device based on the semantic communication and the therapy objectives.

8. A medical therapy delivery system configured to control a treatment delivery device which includes a delivery device processor configured to control treatment delivery structure to delivery therapy, the system comprising:
   a patient monitor including a monitor control processor configured to receive physiological data from medical devices and generate a semantic communication containing at least the physiological data and including a monitor communications device configured to transmit the semantic communication;
   a treatment controller including a controller communications device configured to receive the semantic communication from the patient monitor, a controller memory which stores the physiological data, and one or more controller processors configured to:
      receive treatment delivery settings and objectives of the therapy from a user interface and the physiological data from the controller communication device and the memory,
      communicate with a clinical decision support system to determine best medical practices for a patient with the patient's current physiological or clinical state,
      generate a semantic communication to the delivery device processor with instructions regarding delivery of the treatment, wherein the semantic communication includes an array of primitives and transfer functions describing the relationship of the primitives and the delivered results.

9. The system according to claim 8, wherein the semantic communications further include statements, event summaries, and event tags.

10. The system according to claim 9, wherein
   the primitives are constructed by identifying a driving function for a therapy epoch, an optimizing function for the therapy epoch, and accepted functions for the therapy epoch;
   the statements include at least one of implicit or explicit statements with enumeration and conditional statements relating to the therapy epoch and include the transfer functions relating to the primitives to the delivered results;
   the event summaries are generated from the primitives and the statements and include an intended component and a delivered or resulting component; and
   the event tags are based on one of a harmonized name standard and a manufacturer's declaration.

* * * * *